United States Patent
Wlassics et al.

(10) Patent No.: US 9,732,017 B2
(45) Date of Patent: Aug. 15, 2017

(54) PROCESS FOR THE DEHYDROCHLORINATION OF CHLORINATED HYDROCARBONS

(71) Applicant: SOLVAY SPECIALTY POLYMERS ITALY S.P.A., Bollate (IT)

(72) Inventors: Ivan Wlassics, Garessio (IT); Marco Colladon, Breda di Piave (IT); Stefano Millefanti, Carbonate (IT); Giuseppe Marchionni, Milan (IT); Marco Piccinini, Brussels (BE)

(73) Assignee: SOLVAY SPECIALTY POLYMERS ITALY S.P.A., Bollate (Milan) (IT)

( * ) Notice: Subject to any disclaimer, the term of this patent is extended or adjusted under 35 U.S.C. 154(b) by 0 days.

(21) Appl. No.: 14/909,309

(22) PCT Filed: Jul. 28, 2014

(86) PCT No.: PCT/EP2014/066157
§ 371 (c)(1),
(2) Date: Feb. 1, 2016

(87) PCT Pub. No.: WO2015/014784
PCT Pub. Date: Feb. 5, 2015

(65) Prior Publication Data
US 2016/0176790 A1    Jun. 23, 2016

(30) Foreign Application Priority Data

Aug. 1, 2013  (EP) .................................. 13178905

(51) Int. Cl.
*C07C 17/25* (2006.01)
*C07C 21/08* (2006.01)

(52) U.S. Cl.
CPC .................................. *C07C 17/25* (2013.01)

(58) Field of Classification Search
CPC .............................. C07C 17/25; C07C 21/08
USPC .......................................................... 570/229
See application file for complete search history.

(56) References Cited

U.S. PATENT DOCUMENTS

| | | |
|---|---|---|
| 2,361,072 A | 10/1944 | Vining |
| 2,879,311 A | 3/1959 | Hawkins |
| 2,989,570 A | 6/1961 | Conrad et al. |
| 5,210,344 A | 5/1993 | Reed et al. |

OTHER PUBLICATIONS

Cauvel A. et al., "Monoglyceride Synthesis by Heterogeneous Catalysis Using MCM-41 Type Silicas Functionalized with Amino Groups", J. Org. Chem., 1997, vol. 62(3), p. 749-751—American Chemical Society.
Sercheli R. et al., "Encapsulation of N,N',N''-tricyclohexylguanidine in hydrophobic zeolite Y: Synthesis and catalytic activity", Tetrahedron Letters, 1997, vol. 38(8), p. 1325-1328—Elsevier Science Ltd.

*Primary Examiner* — Jafar Parsa

(57) ABSTRACT

A process for the dehydrochlorination of a chlorinated hydrocarbon comprising at least one chlorine atom and at least one hydrogen atom on vicinal carbon atoms to yield the corresponding unsaturated hydrocarbon, said process comprising contacting the chlorinated hydrocarbon with a guanidinium salt or its guanidine precursor.

16 Claims, No Drawings

PROCESS FOR THE DEHYDROCHLORINATION OF CHLORINATED HYDROCARBONS

CROSS-REFERENCE TO RELATED APPLICATION

This application is a U.S. national stage entry under 35 U.S.C., §371 of International Application No. PCT/EP2014/066157 filed Jul. 28, 2014, which claims priority to European application No. 13178905.9 filed on Aug. 1, 2013. The entire contents of these applications are explicitly incorporated herein by this reference.

TECHNICAL FIELD

The invention relates to a process for the manufacture of unsaturated compounds by catalytic dehydrochlorination of chlorinated hydrocarbons, in particular to a process for the manufacture of vinylidene chloride.

BACKGROUND ART

The dehydrochlorination of chlorinated hydrocarbons for the preparation of unsaturated compounds is a common synthetic process at industrial level.

For instance, vinylidene chloride is prepared commercially by the dehydrochlorination of 1,1,2-trichloroethane using calcium or sodium hydroxide. The process produces vinylidene chloride in very high yields (approximately 90%) but has the drawback that great amounts of inorganic by-products (e.g. $CaCl_2$ or NaCl) are generated and need to be disposed of or recycled. Catalytic processes producing hydrogen chloride as by-product would therefore be more advantageous.

U.S. Pat. No. 2,361,072 (DU PONT) Oct. 24, 1944 relates to a process for the manufacture of trichloroethylene by reaction of tetrachloroethane with a nitrogen base. Diorthotolyl guanidine is mentioned on page 1, right-hand column, line 32; this is the sole guanidine base in a list of different nitrogen bases. The examples teach the use of triethylamine and quinolone.

The use of certain amines or their salts in the dehydrochlorination reaction of chlorinated hydrocarbons has been previously disclosed.

U.S. Pat. No. 2,879,311 (THE DISTILLERS COMPANY LIMITED) Mar. 24, 1959 discloses a process for the dehydrochlorination of 1,2,3-trichlorobutane carried out in the presence of the hydrochloride or ammonium chloride salt of an amine having a pK in the range of 3.0 to 9.0. Exemplary amines suitable for the preparation of the salt are preferably tertiary amines such as: alpha- and gamma-picoline, 2,4,6-collidine, 5-ethyl-2-methyl-pyridine, tri-n-butylamine, pyridine, quinoline, N-ethylpyperidine, cyclohexylamine.

U.S. Pat. No. 2,989,570 (ETHYL CORPORATION) Jun. 20, 1961 discloses a process for the preparation of vinylidene chloride by dehydrochlorination of 1,1,2-trichloroethane in the presence of an amine, its hydrochloric or quaternary ammonium chloride salt. The amine is selected among those amines having a $pK_b$ (wherein $K_b$ indicates the basic dissociation constant) of less than 7. Diphenylguanidine is listed among the suitable amines to be used in the process. The examples provided however do not indicate the existence of a catalytic process, rather of a stoichiometric reaction.

U.S. Pat. No. 5,210,344 (THE DOW CHEMICAL COMPANY) May 11, 1993 discloses a process for the preparation of vinylidene chloride by dehydrochlorination of 1,1,2-trichloroethane in the presence of a cyclic amine having a $pK_a$ greater than 11. Exemplary cyclic amines with a $pK_a$ greater than 11 are 2,2,6,6-tetramethylpiperidine, 1,2,2,6,6-pentamethylpiperidine, 2,2,4-trimethylpiperidine, 1,8-diazabicyclo-[5.4.0]-undec-7-ene, and 1,5-diazabicyclo-[4.3.0]-non-5-ene.

It has now been found that the use of certain guanidinium salts or their guanidine precursors provides sustainable catalytic processes for the dehydrochlorination of chlorinated hydrocarbons to produce unsaturated compounds in good yields. The use of said guanidinium salts, or their guanidine precursors, in the dehydrochlorination reaction of 1,1,2-trichloroethane is selective in the production of vinylidene chloride thereby reducing the amount of by-products. Hydrogen chloride generated in the process may be easily recovered in anhydrous form.

SUMMARY OF INVENTION

Object of the invention is a process for the dehydrochlorination of a chlorinated hydrocarbon comprising at least one chlorine atom and at least one hydrogen atom on vicinal carbon atoms to yield the corresponding unsaturated hydrocarbon, said process comprising contacting the chlorinated hydrocarbon with a guanidinium salt or its guanidine precursor which is selected from the group of compounds of formula (I):

wherein each of R, $R^1$, $R^2$, $R^3$ and $R^4$ is independently selected from the group consisting of H, $C_1$-$C_{12}$ linear or branched alkyl, optionally substituted; and wherein each of R, $R^1$, $R^2$ and $R^3$ may be comprised in an aliphatic or aromatic cyclic structure, optionally containing heteroatoms; and wherein each of $R^1$, $R^2$, $R^3$ and $R^4$ may be a monocyclic or polycyclic aromatic radical optionally substituted and/or optionally containing heteroatoms.

The expression "vicinal carbon atoms" is used herein in its generally recognized meaning to indicate two adjacent carbon atoms. Thus the chlorinated hydrocarbon comprises at least one chlorine atom bound to a first carbon atom and at least one hydrogen atom bound to a carbon atom adjacent to the first.

Any chlorinated hydrocarbon which possesses at least one chlorine atom and at least one hydrogen atom on vicinal carbon atoms may be dehydrochlorinated using the process of the invention.

Typically, the chlorinated hydrocarbon is selected from the group of compounds of formula (II):

$$R_h R_{h1} CCl\text{---}CHR_{h2} R_{h3} \quad (II)$$

and the corresponding unsaturated hydrocarbon obtained by the dehydrochlorination process is a compound of formula (III):

$$R_h R_{h1} C{=}CR_{h2} R_{h3} \quad (III).$$

In formulas (II) and (III) each of $R_h$, $R_{h1}$, $R_{h2}$ and $R_{h3}$ is independently selected from the group consisting of H, Cl, $C_1$-$C_{10}$ optionally fluorinated alkyl. Typically each of $R_h$, $R_{h1}$, $R_{h2}$ and $R_{h3}$ is independently selected from the group consisting of H, Cl, $C_1$-$C_5$ alkyl.

In an embodiment of the process of the invention $R_h$ and $R_{h2}$ are simultaneously hydrogen.

In an advantageous aspect of said embodiment $R_{h1}$ and $R_{h3}$ are selected from the group consisting of H and Cl. Preferably when $R_{h1}$ is H then $R_{h3}$ is Cl and the compound of formula (III) is vinyl chloride.

In a preferred embodiment of the invention compound of formula (II) is 1,1,2-trichloroethane, that is $R_{h1}=R_{h3}=H$ and $R_h=R_{h2}=Cl$, and compound of formula (III) is vinylidene chloride.

The process of the invention is carried out by contacting the chlorinated hydrocarbon with the guanidine precursor or, preferably, with the guanidinium salt.

Non-limiting examples of suitable guanidinium salts include: hydrohalogenides, such as hydrofluoride, hydrochloride, hydrobromide, hydroiodide, carbonates, nitrates, phosphates, sulfates, fluoroalkylsulfates of formula $R_fSO_3^-$, wherein $R_f$ is a $C_1$-$C_{12}$ fluoroalkyl, optionally comprising oxygen atoms, e.g. $CF_3SO_3^-$. The guanidinium hydrochloride salt is preferred.

The guanidine precursor suitable for the inventive process is selected from the group consisting of the compounds of formula (I):

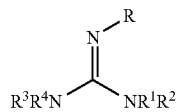

(I)

wherein each of R, $R^1$, $R^2$, $R^3$ and $R^4$ is independently selected from the group consisting of H, $C_1$-$C_{12}$ linear or branched alkyl, optionally substituted; and wherein R, $R^1$, $R^2$ and $R^3$ may be comprised in an aliphatic or aromatic cyclic structure, optionally containing heteroatoms; and wherein $R^1$, $R^2$, $R^3$ and $R^4$ may be a monocyclic or polycyclic aromatic radical, optionally substituted and/or optionally containing heteroatoms.

In a first embodiment, group R in formula (I) is H and each of $R^1$, $R^2$, $R^3$ and $R^4$ is independently selected from the group consisting of H, $C_1$-$C_{12}$ linear or branched, optionally substituted alkyl, and monocyclic or polycyclic aromatic radical, optionally substituted and/or optionally containing heteroatoms. Notable non-limiting examples of guanidines belonging to this embodiment are compounds selected from the group consisting of tetramethylguanidine, wherein $R^1=R^2=R^3=R^4=CH_3$, and the compounds wherein $R^1=R^2=R^3=H$ and $R^4$ is selected from the group consisting of monocyclic or polycyclic aromatic radicals, optionally substituted and/or optionally containing heteroatoms. $R^4$ may be for instance benzimidazole. Preferably, $R^1$, $R^2$, $R^3$ and $R^4$ are not simultaneously H.

Non-limiting examples of further suitable guanidine precursors of formula (I) wherein R, $R^1$, $R^2$ and $R^3$ are comprised in an aliphatic or aromatic cyclic structure, optionally containing heteroatoms may be selected from the group consisting of formulae (G-1) and (G-2) herein below:

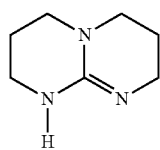

G-1

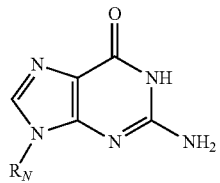

G-2 wherein $R_N$ in formula (G-2) is H or a $C_1$-$C_{12}$ linear or branched, optionally substituted alkyl.

The guanidine precursor is preferably selected form the group consisting of tetramethylguanidine and 1,5,7-triazabicyclo[4.4.0]-dec-5-ene (compound of formula G-1).

In an embodiment of the invention the guanidine precursor or the guanidinium salt may be supported on an inert support thereby providing a heterogeneous catalyst. The guanidinium salt or its guanidine precursor may either be physically adsorbed on the inert support or chemically anchored to its surface according to methods well known in the art. Non-limiting examples of suitable supports are for instance silica, $TiO_2$, $Al_2O_3$, $SiO_2/Al_2O_3$, zeolites, mesoporous silicas (e.g. MCM-41). Suitable techniques for the preparation of supported guanidinium salts, or precursors thereof, are those described in CAUVEL, A., et al. Monoglyceride synthesis by heterogeneous catalysis using MCM-41 type silicas functionalized with amino groups. *J. Org. Chem.* 1997, vol. 62, p. 749-751. and in SERCHELI, R., et al. Encapsulation of N,N',N''-tricyclohexylguanidine in hydrophobic zeolite Y: Synthesis and catalytic activity. *Tetrahedron Lett.* 1997, vol. 38, p. 1325-1328.

It has been found that the active catalytic species in the inventive process is the guanidinium salt. In a first non-catalytic step of the process, however, the guanidine precursor is transformed into the hydrochloride guanidinium salt by reaction with one equivalent of the chlorinated hydrocarbon, thereby generating the catalytic species in situ.

Guanidinium salts suitable for the inventive process are characterised by the fact that they have a $pK_b$ which is higher than the $pK_b$ of the guanidine precursor but still have a sufficiently basic character to abstract HCl from the chlorinated hydrocarbon present in the reaction mixture.

Suitable guanidine precursors are in general characterised by $pK_b$ of less than 9, typically of less than 7, more typically of less than 5. The term $pK_b$ indicates the negative base-10 logarithm of the basic dissociation constant ($K_b$) of the guanidine precursor.

Advantageously, per each equivalent of guanidinium salt at least one equivalent of chlorinated hydrocarbon is converted into the corresponding unsaturated compound and at least one equivalent of HCl is generated. Preferably, per each equivalent of guanidinium salt more than one equivalent of chlorinated hydrocarbon is converted into the corresponding unsaturated compound and more than one equivalent of HCl is generated.

For instance, when tetramethylguanidine is used as the precursor of the catalytic species, at least 1.6 moles of HCl are extracted per mole of guanidinium salt, that is 2.6 moles of HCl per mole of the tetramethylguanidine precursor.

Similarly, when 1,5,7-triazabicyclo[4.4.0]-dec-5-ene is used as the guanidine precursor, 1.65 moles of HCl are extracted per mole of guanidinium salt, that is 2.65 moles of HCl per mole of the precursor.

The HCl generated in the process, in excess of the amount of HCl required to form the guanidinium hydrochloride salt when the guanidine precursor is used in the process, generally coordinates the guanidinium salt. The coordination product of the guanidinium salt and HCl will be hereinafter referred to as "Guanidinium salt:HCl". The HCl removed from the chlorinated hydrocarbon is typically released from the coordination with the guanidinium salt by heating.

Accordingly, when the guanidinium precursor is used to initiate the dehydrochlorination process, said process will comprise a step wherein the guanidinium precursor reacts with one equivalent of the chlorinated hydrocarbon forming the corresponding unsaturated compound and one equivalent of the guanidinium hydrochloride salt. In the subsequent steps, the guanidinium salt will further react with the chlorinated hydrocarbon forming the corresponding unsaturated compound and the coordination product Guanidinium salt:HCl. The amount of HCl coordinated by the guanidinium salt in the coordination product will depend on the nature of the guanidine precursor.

Advantageously, the process comprises the steps of: heating the coordination product of the guanidinium salt and HCl, Guanidinium salt:HCl, to a temperature suitable to release HCl; and separating HCl from the guanidinium salt. Once recovered, the guanidinium salt may be recycled into the inventive process.

An advantage of the inventive process is that many catalytic cycles can be performed with the same initial amount of guanidinium salt (or its precursor), thereby providing a high productivity process for the dehydrochlorination of chlorinated hydrocarbons.

Typically, the guanidinium salt and the chlorinated hydrocarbon are contacted in a mole ratio from 1:100 to 100:1, preferably from 1:50 to 50:1, more preferably from 1:10 to 10:1.

The gaseous HCl produced in the process may be recovered by any means known in the art. An advantage of the process is that HCl is produced in substantially anhydrous form.

The temperature at which HCl is released from the coordination product Guanidinium salt:HCl and the guanidinium salt regenerated, hereinafter referred to as "HCl release temperature" depends on the guanidinium salt.

Typically, the HCl release temperature is greater than 100° C., generally greater than 120° C. The HCl release temperature generally does not exceed 250° C., even it does not exceed 230° C.

The steps of heating the coordination product Guanidinium salt:HCl and separating the generated HCl can be carried out at the same time as the dehydrochlorination process or in a separate stage.

In a first embodiment of the process, the release of HCl and the regeneration of the guanidinium salt are carried out simultaneously with the dehydrochlorination process by operating the process at a temperature equal to or higher than the HCl release temperature of the guanidinium salt employed.

Accordingly by operating the dehydrochlorination process at a temperature equal to or higher than the HCl release temperature and by continuously removing HCl from the system, the catalytically active species is continuously regenerated in the reaction mixture and long reaction times, with consequent high productivity, can be achieved.

For instance, when the guanidinium salt is tetramethylguanidinium chloride the HCl release temperature is equal to or greater than 145° C. An advantageous range of temperatures for carrying out the dehydrochlorination process according to the first embodiment is thus a temperature equal to or greater than 145° C., preferably a temperature in the range from 145° C. to 180° C., more preferably in the range from 145° C. to 175° C.

When the guanidinium salt is the hydrochloride salt of 1,5,7-triazabicyclo[4.4.0]-dec-5-ene the HCl release temperature is equal to or greater than 170° C. Consequently, a process according to the first embodiment using 1,5,7-triazabicyclo[4.4.0]-dec-5-ene as the guanidine precursor is preferably carried out at a temperature equal to or greater than 170° C., more preferably from 170° C. to 195° C., even more preferably from 170° C. to 185° C.

The optimal temperature for carrying out the process can be determined on the basis of the guanidine precursor or the guanidinium salt by a person skilled in the art using common experimentation.

In an alternative embodiment of the inventive process the steps of releasing HCl from the coordination product Guanidinium salt:HCl and regenerating the guanidinium salt are carried out in a separate stage with respect to the dehydrochlorination process. In such an embodiment the dehydrochlorination process of the chlorinated hydrocarbon is carried out at a temperature lower than the HCl release temperature of the guanidinium salt. The coordination product Guanidinium salt:HCl is then separated from the reaction mixture and then heated to a temperature equal to or higher than the HCl release temperature, thereby liberating HCl and regenerating the guanidinium salt. The guanidinium salt can then be recycled into the process for a further dehydrochlorination cycle.

The process is typically carried out at atmospheric pressure and in any event at a pressure of at most 0.5 MPa.

The process is typically carried out in the liquid phase, generally in the presence of a solvent. Suitable solvents are aprotic solvents. Notable examples of suitable solvents are organic solvents selected from the group consisting of ketones, sulphoxides, like dimethylsulfoxide, sulfones, like dimethylsulfone, amides, like N,N-dimethylformamide, N,N-dimethylacetamide, pyrrolidones, like N-methylpyrrolidone, N-ethylpyrrolidone, and ethers, like tetraethyleneglycol dimethyl ether (tetraglyme).

Advantageous results were obtained using solvents selected from the group consisting of N,N-dimethylformamide, N,N-dimethylacetamide, tetraethyleneglycol dimethyl ether, dimethylsulfoxide. Particularly advantageous results were obtained using dimethylsulfoxide as a solvent.

Another class of suitable solvents for the inventive process is represented by so-called ionic liquids, that is salts which melt without decomposing, thereby forming a liquid at a given temperature. Preferred ionic liquids for the use as solvents in the inventive process are those which are liquid at temperatures of 250° C. or less, more preferably at temperatures of 200° C. or less. Most preferred are ionic liquids which are in the liquid state at room temperature or even below. Furthermore, preferred ionic liquids are those which have a very low vapor pressure. Suitable ionic liquids are preferably selected among those inert toward the substances participating in the reaction. Examples include compounds like 1-butyl-3-methyl imidazolium chloride, methyl trioctyl ammonium chloride, tetrabutyl ammonium chloride.

The process may be carried out batch-wise or in continuous using equipment known in the art.

The process of the invention may additionally comprise a step wherein by-products of the dehydrochlorination reaction, typically consisting of unsaturated chlorinated hydrocarbons, are separated from the liquid phase and recycled into the process, optionally after an intermediate step.

As an example of this further embodiment of the inventive process, mention may be made of the recovery and reuse of 1,2-dichloroethylene (cis and trans isomer) which is formed as a by-product in the dehydrochlorination reaction of 1,1,2-trichoroethane to vinylidene chloride. 1,2-dichloroethylene may be separated from the reaction mixture and vinylidene chloride by distillation, or any other conventional technique known in the art. Once isolated, 1,2-dichloroethylene may be converted back into 1,1,2-trichoroethane by hydrochlorination in the presence of a suitable catalyst, e.g. $AlCl_3$. It can then be recycled back into the inventive process.

The invention will be now described in more detail with reference to the following examples whose purpose is merely illustrative and not (imitative of the scope of the invention.

Should the disclosure of any patents, patent applications, and publications which are incorporated herein by reference conflict with the description of the present application to the extent that it may render a term unclear, the present description shall take precedence.

EXAMPLES

General Procedure for the Dehydrochlorination of 1,1,2-trichloroetane to Vinylidene Chloride The guanidinium salt (or the guanidine precursor) and the solvent (50 mL) were placed in a 100 mL glass, 4-necked round-bottomed flask reactor equipped with a magnetic stirrer, a condenser, a thermometer, a digital $N_2$ flow control apparatus and a syringe pump equipped with a polypropylene or glass syringe and a PTFE feeding line and needle. The apparatus further comprised a graduated Pyrex test tube immersed in a Dewar containing a dry-ice/acetone slurry (T=−78° C.) connected to the reactor condenser head by means of a PTFE feeding line for the recovery of the gaseous reaction products.

The reactor was purged with $N_2$ for 30 minutes at 20° C., the condenser is cooled to −10° C. and the $N_2$ flow set at a rate of 0.6 N-L/h. The stirring rate was set at 1000 rpm. 1,1,2-trichloroethylene was added to the heterogeneous reaction mixture at a fixed rate of 0.2 mL/h (2.154 mmoles/h) with the syringe pump. The glass reactor was dipped in an oil bath and heated to a temperature equal to or greater than the HCl release temperature determined for the guanidine precursor with a stirring rate of 1000 rpm. Total reaction time was recorded with regular intermediate samplings. At the end of each reaction period, the reaction products were analyzed and identified by quantitative $^1$H-NMR, GC and GC-MS analysis.

The results were analyzed in order to determine: rate constant of the $1^{st}$ order catalytic reaction ($k_C$; dehydrochlorination promoted by guanidinium salt); total conversion of 1,1,2-trichloroethane ($C_{112TCE}$); selectivity in vinylidene chloride formation in the catalytic process ($S_{VDC}$). All results are summarized in Table 1.

Examples 1-3: Dehydrochlorination with Tetramethylguanidinium Hydrochloride (TMGNH$_2$(+)Cl(−))

Following the General Procedure, dehydrochlorination of 1,1,2-trichloroethylene was carried out in the presence of tetramethylguanidinium chloride in three different solvents: tetraglyme, dimethylsulfoxide (DMSO) and 1-butyl-3-methyl imidazolium chloride under the following experimental conditions:

Ex. 1: tetraglyme; TMGNH$_2^{(+)}$Cl$^{(-)}$: 12.45 mmoles; reaction temperature: 177° C.; reaction time: 48.5 h.

Ex. 2: DMSO (120 mL); TMGNH$_2^{(+)}$Cl$^{(-)}$: 36 mmoles; reaction temperature: 150° C.; reaction time: 7.5 h.

Ex. 3: 1-butyl-3-methyl imidazolium chloride ([C$_4$mim]Cl) (124 mL); TMGNH$_2^{(+)}$Cl$^{(-)}$: 36 mmoles; reaction temperature: 177° C.; reaction time: 18 h.

The $1^{st}$ order catalytic reaction rate constants, selectivities in vinylidene chloride and conversions of 1,1,2-trichloroethylene are reported in Table 1.

Example 4: Dehydrochlorination with 1,5,7-triazabicyclo[4.4.0]dec-5-ene (TBD) in Tetraglyme Following the General Procedure, dehydrochlorination of 1,1,2-trichloroethylene was carried out in the presence of 1,5,7-triazabicyclo[4.4.0]dec-5-ene (12.45 mmoles) as the guanidine precursor in tetraglyme as the solvent. The reaction temperature was set at 170° C. and the reaction was monitored for 30 h. The reaction rate constants, selectivity in vinylidene chloride and conversion of 1,1,2-trichloroethylene are reported in Table 1.

Example 5: Dehydrochlorination with 1,5,7-triazabicyclo[4.4.0]dec-5-ene Supported on SiO$_2$ in Tetraglyme Supported 1,5,7-triazabicyclo[4.4.0]dec-5-ene was prepared according to a modification of the procedure disclosed in CAUVEL, A., et al. Monoglyceride synthesis by heterogeneous catalysis using MCM-41 type silicas functionalized with amino groups. *J. Org. Chem.* 1997, vol. 62, p. 749-751.

The dehydrochlorination process was carried out following the General Procedure employing the supported guanidine precursor (12.45 g, 12.45 mmoles, 1 mmol TBD/1 g silanized support) in tetraglyme (50 mL) at 182° C. for 30 h total reaction time. The results are reported in Table 1.

Comparative Example 1 and 2: Dehydrochlorination with Triethylamine (TEA) or 1,8-Diazabicyclo[5.4.0]undec-7-ene (DBU) in Tetraglyme Following the General Procedure, dehydrochlorination of 1,1,2-trichloroethylene was carried out replacing the guanidine precursor with triethylamine (CE1: 12.45 mmol; reaction temperature 130-135° C.; reaction time: 30 h) or with 1,8-diazabicyclo[5.4.0]undec-7-ene (CE2: 12.45 mmoles; reaction temperature 190° C.; reaction time: 30 h). Results are reported in Table 1.

TABLE 1

| Example | Precursor/ solvent | $k_C$ (min$^{-1}$) | $C_{112TCE}$ (mol %) | $S_{VDC}$ (mol %) |
|---|---|---|---|---|
| Ex.1 | TMGNH$_2^{(+)}$Cl$^{(-)}$/ tetraglyme | 0.0121 | 78 | 62 |
| Ex.2 | TMGNH$_2^{(+)}$Cl$^{(-)}$/ DMSO | 0.1 | 95 | 85 |
| Ex. 3 | TMGNH$_2^{(+)}$Cl$^{(-)}$/ ([C$_4$mim]Cl | | 55 | 48 |
| Ex. 4 | TBD/tetraglyme | 0.012 | 83 | 60 |
| Ex. 5 | supported TBD/ tetraglyme | 0.095 | 60 | 61 |
| CEx. 1 | TEA/tetraglyme | 0.0 | 28* | 96* |
| CEx. 2 | DBU/tetraglyme | 0.0059 | 78 | 55 |

*Selectivity and conversion obtained with non-catalytic process

When the dehydrochlorination process is carried out in the presence of triethylamine conversion of 1,1,2- trichloroethane to vinylidene chloride takes place stoichiometrically. Once all the triethylamine has reacted, forming the triethyl ammonium chloride salt, the process stops.

The dehydrochlorination process proceeds catalytically in the presence of 1,8-diazabicyclo[5.4.0]undec-7-ene. However, as can be seen by comparing the rate constant data of Comparative Example 2 with those of Example 1 or Example 4, the use of a guanidinium salt in the dehydrochlorination process affords much higher conversion rates without loss of selectivity in the final product.

The invention claimed is:

1. A process for the dehydrochlorination of a chlorinated hydrocarbon comprising at least one chlorine atom and at least one hydrogen atom on vicinal carbon atoms to yield the corresponding unsaturated hydrocarbon, said process comprising contacting the chlorinated hydrocarbon with a guanidinium salt or its guanidine precursor wherein the guanidine precursor is selected from the group of compounds of formula (I):

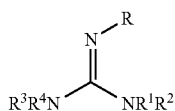

(I)

wherein each of R, $R^1$, $R^2$, $R^3$ and $R^4$ is independently selected from the group consisting of H and $C_1$-$C_{12}$ linear or branched alkyl, optionally substituted; or wherein R, $R^1$, $R^2$ and $R^3$ may be comprised in an aliphatic or aromatic cyclic structure, optionally containing heteroatoms; or wherein $R^1$, $R^2$, $R^3$ and $R^4$ may be a monocyclic or polycyclic aromatic radical optionally containing heteroatoms and/or optionally substituted.

2. The process according to claim 1 wherein the guanidinium salt forms a coordination product with HCl produced in the dehydrochlorination reaction.

3. The process according to claim 2 further comprising the steps of: heating the coordination product of the guanidinium salt with HCl to a temperature suitable to release HCl; and separating HCl from the guanidinium salt.

4. The process according to claim 2, wherein the process is carried out at a temperature equal to or higher than the temperature suitable to release HCl from the coordination product of the guanidinium salt with HCl.

5. The process according to claim 2, wherein the process is carried out at a temperature lower than the temperature suitable to release HCl from the coordination product of the guanidinium salt with HCl and wherein the process further comprises the steps of separating said coordination product before performing the step of heating to a temperature suitable to release HCl; and separating HCl from the guanidinium salt.

6. The process according to claim 5 further comprising the step of reusing the guanidinium salt into the dehydrochlorination step of the process.

7. The process according to claim 1, wherein the chlorinated hydrocarbon is selected from the compounds of formula (II): $R_hR_{h1}CCl$—$CHR_{h2}R_{h3}$ wherein each of $R_h$, $R_{h1}$, $R_{h2}$ and $R_{h3}$ is independently selected from the group consisting of H, Cl, and $C_1$-$C_{10}$ optionally fluorinated alkyl.

8. The process according to claim 7 wherein $R_{h1}$=$R_{h3}$=H and $R_h$=$R_{h2}$=Cl and the corresponding unsaturated hydrocarbon is vinylidene chloride.

9. The process according to claim 1, wherein R is H and each of $R^1$, $R^2$, $R^3$ and $R^4$ is independently selected from the group consisting of H, $C_1$-$C_{12}$ linear or branched, optionally substituted alkyl, and monocyclic or polycyclic aromatic radical optionally substituted and/or optionally containing heteroatoms.

10. The process according to claim 1, wherein $R^1$=$R^2$=$R^3$=$R^4$=$CH_3$.

11. The process according to claim 1, wherein the guanidine precursor of formula (I) is selected from the consisting of compounds of formulae (G-1) and (G-2):

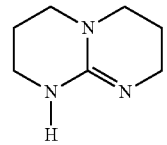

G-1

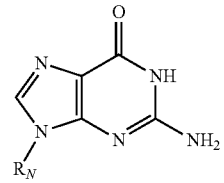

G-2 wherein $R_N$ in formula (G-2) is H or a $C_1$-$C_{12}$ linear or branched, optionally substituted, alkyl.

12. The process according to claim 1, wherein the process is carried out in liquid phase in the presence of a solvent.

13. The process according to claim 12 wherein the solvent is selected from the group consisting of ketones, sulphoxides, sulfones, amides, pyrrolidones, ethers, and ionic liquids.

14. The process according to claim 3, wherein the process is carried out at a temperature equal to or higher than the temperature suitable to release HCl from the coordination product of the guanidinium salt with HCl.

15. The process according to claim 3, wherein the process is carried out at a temperature lower than the temperature suitable to release HCl from the coordination product of the guanidinium salt with HCl and wherein the process further comprises the steps of separating said coordination product before performing the step of heating to a temperature suitable to release HCl; and separating HCl from the guanidinium salt.

16. The process according to claim 15 further comprising the step of reusing the guanidinium salt into the dehydrochlorination step of the process.

* * * * *